(12) United States Patent
Helf et al.

(10) Patent No.: US 6,706,988 B1
(45) Date of Patent: Mar. 16, 2004

(54) SWITCH ACTUATING MECHANISM AND ELECTRICALLY CONTROLLED DEVICE USING SAME

(75) Inventors: Thomas A. Helf, New Berlin, WI (US); Tyler D. Duston, Evanston, IL (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 10/290,913

(22) Filed: Nov. 8, 2002

(51) Int. Cl.⁷ .......................... H01H 3/02; H01H 15/00
(52) U.S. Cl. .................. 200/553; 200/332; 200/547; 200/561
(58) Field of Search .............. 200/16 R–16 F, 200/43.01–43.22, 329–332, 553–563, 564, 567, 572

(56) References Cited

U.S. PATENT DOCUMENTS

| | | | |
|---|---|---|---|
| 3,661,323 A | | 5/1972 | Farris ........................ 236/93 |
| 3,922,510 A | * | 11/1975 | Arthur ....................... 200/332 |
| 3,993,881 A | * | 11/1976 | Marsilio ..................... 200/450 |
| 3,997,917 A | * | 12/1976 | Kihara ....................... 235/480 |
| 4,705,920 A | * | 11/1987 | Sahrbacker ................ 200/43.04 |
| 4,804,821 A | | 2/1989 | Glucksman .................. 219/271 |
| 5,115,975 A | | 5/1992 | Shilling ..................... 239/55 |
| 5,378,863 A | * | 1/1995 | Sekita ....................... 200/16 R |
| 5,547,616 A | | 8/1996 | Dancs et al. ................. 261/26 |
| 5,555,973 A | * | 9/1996 | Horisawa .................... 200/561 |

* cited by examiner

Primary Examiner—James R. Scott

(57) ABSTRACT

An automated device (10) has a curved outer cover (12) through which a switch arm (48) extends. The switch arm is pivotally supported inside the cover and is connected therein by means of a lost motion mechanism (51) to a switch actuator (46) of a switch (44) to control operation of the switch.

14 Claims, 2 Drawing Sheets

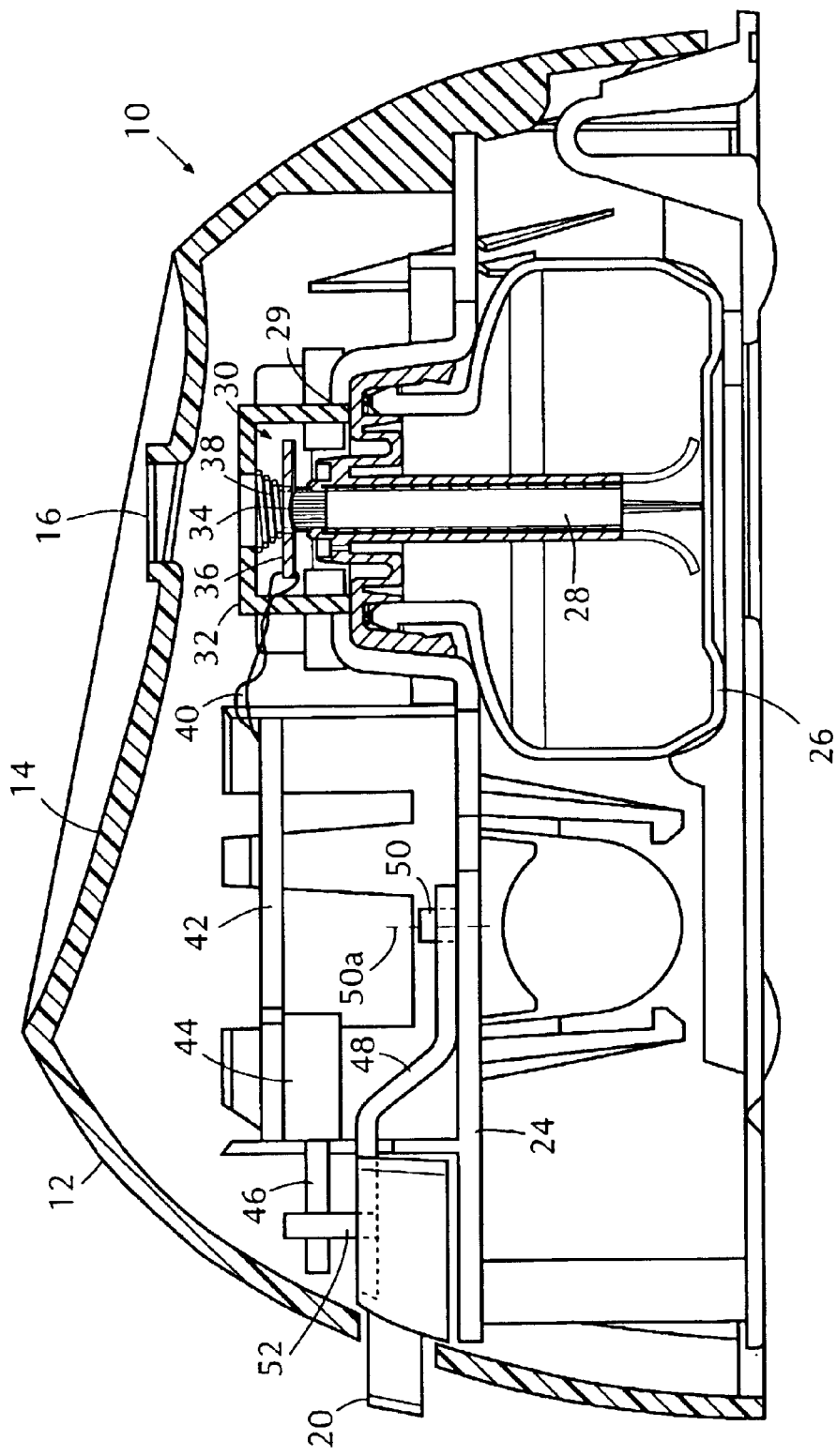

SWITCH ACTUATING MECHANISM AND ELECTRICALLY CONTROLLED DEVICE USING SAME

BACKGROUND OF THE INVENTION

1. Field of the Invention

This invention relates to the control of electrically powered devices such as piezoelectrically driven atomizer devices; and more particularly it concerns novel switch actuator mechanisms for controlling the operation of said devices.

2. Description of the Related Art

Many electrically controlled devices have been developed for producing desired mechanical effects and whose operation is controlled by operation of a button or actuator which is mounted on an outer cover of the device. By way of example, battery driven atomizers and aroma distributors are described in U.S. Pat. No. 5,547,616, No. 5,115,975, No. 4,804,821 and No. 3,661,323. These devices have, in most cases, an outer cover in which the atomizer or aroma distributor mechanism is mounted and whose operation is controlled by an electrical switch having a moveable switch element mounted on the outer cover.

The outer cover in many of these devices does not have sufficient strength to hold the moveable switch element securely without extra reinforcement. Further, the outer cover is often curved so that the moveable switch element must follow a curved path. This precludes the use of multiposition switches which have linearly moveable switch elements.

SUMMARY OF THE INVENTION

This invention in one aspect provides a novel switch actuating mechanism which comprises an elongated switch arm which is pivotally mounted near one end thereof on a support, a switch having a switch element which is moveable along a linear path, the switch being mounted in a fixed position relative to the support, and a lost motion interconnection between the switch arm and the switch element. The lost motion interconnection permits relative movement between the switch arm and the switch element in a direction perpendicular to the linear path but prevents relative movement in a direction parallel to that path. As a result, pivotal movement of the switch arm produces linear movement of the switch element.

In another aspect, the invention provides a novel electrically controlled device which comprises a mechanism for producing a desired result and an electrical circuit with a multi-position switch for controlling operation of the mechanism. The switch has a switch element that is moveable through a given range along a linear path; and the switch and switch element are mounted on a support structure within a shell-like outer cover that has a curved outer surface. An elongated switch arm is pivotally connected at one end to the support structure inside the outer cover such that said switch arm pivots about an axis that is perpendicular to the linear path of the switch element and such that the switch arm can swing through an arc that includes the given range of movement of the switch element. A lost motion mechanical interconnection is provided between the switch arm and the switch element and is located within the outer cover. The lost motion interconnection permits relative movement between the switch arm and the switch element in a direction perpendicular to the linear path but prevents relative movement in a direction parallel to that path. Thus, while the switch arm is supported solidly within, and not by, the outer cover, its movement follows the curved surface of the cover. At the same time, this curved movement causes the switch element to be moved along its linear path. The switch arm extends beyond the lost motion interconnection and out through a slot in the outer cover where it can be operated.

BRIEF DESCRIPTION OF THE DRAWINGS

FIG. 3 is an elevational section view taken along line 3—3 of FIG. 2.

DETAILED DESCRIPTION OF THE PREFERRED EMBODIMENT

Figure 1:
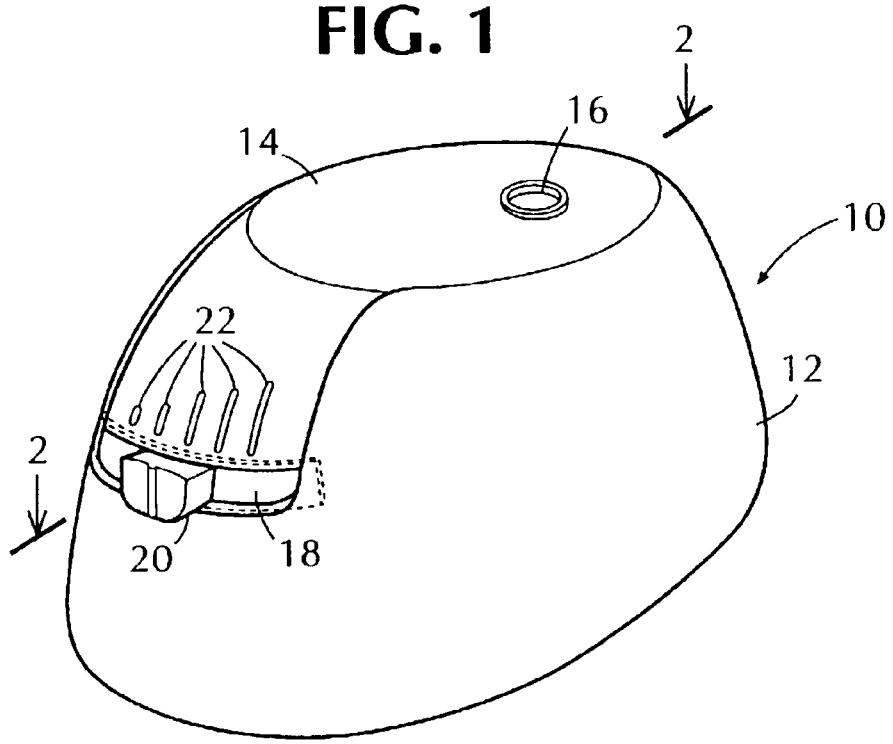
FIG. 1 is a perspective view of an atomizer device according to the invention.

As seen in FIG. 1, an atomizer device 10 according to the invention has a shell-like outer cover 12 which is somewhat egg-shaped, but it is flattened on the bottom and it has a shallow dished upper region 14 formed in the top. An ejection opening 16 is provided in the dished upper region 14. Atomized liquid droplets produced by the atomizer device 10 are ejected through the opening 16. A horizontal slot 18 is formed in a curved front surface of the outer cover 12; and a switch actuator button 20 moves along the slot 18. The button 20 can be set to any of several positions, indicated by vertical lines 22 on the cover 12, to adjust the intensity of atomization produced by the device 10.

Figure 2:
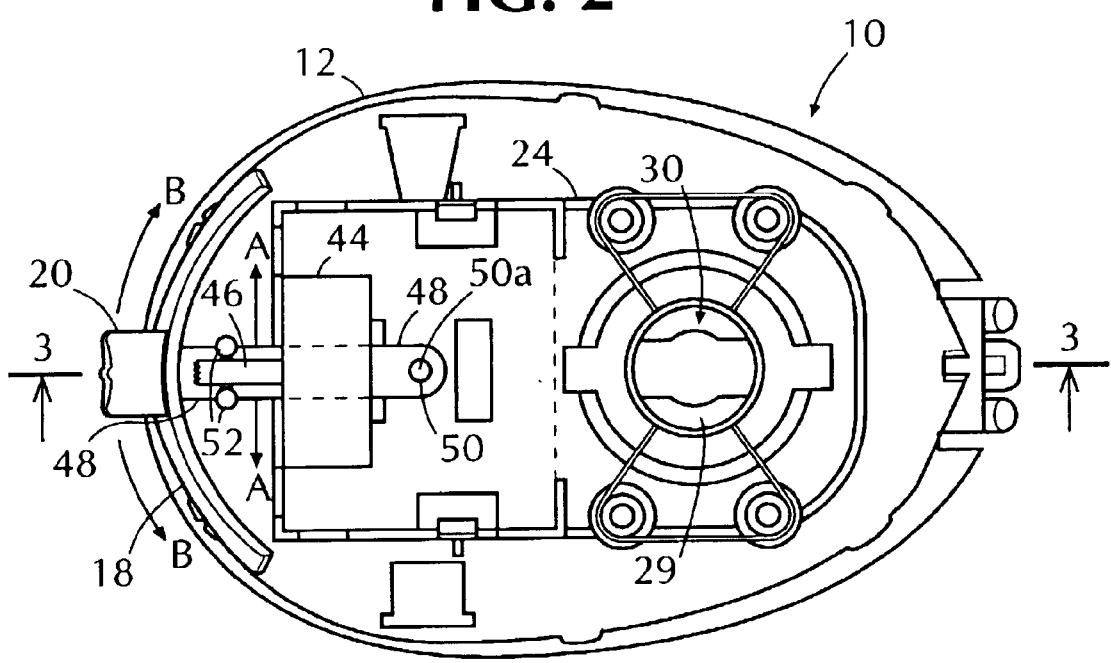
FIG. 2 is a plan section view taken along line 2—2 of FIG. 1.

As can be seen in FIGS. 2 and 3, a support chassis 24 extends horizontally within the outer cover 12. The chassis 24 supports on its underside a liquid reservoir or bottle 26 (FIG. 3) which contains a liquid to be atomized. Liquid from the bottle 26 rises up out of the bottle by the capillary action of a wick 28 which extends through an opening 29 in the chassis. An atomization assembly 30 is mounted on the upper side of the chassis above the opening 29 and the reservoir or bottle 26. The atomization assembly includes a retainer 32 which is supported on the upper side for the chassis over the opening 29. The retainer 32 contains an orifice plate 34 and a piezoelectric actuator 36 which vibrates the orifice plate. The orifice plate 34 is pushed down against the top of the wick 28 by a spring 38 so that liquid from the bottle 26 will be supplied to the underside of the plate and will pass through its orifices and become ejected in the form of minute liquid droplets as the plate is vibrated by the piezoelectric actuator 36.

As also shown in FIG. 3, the actuator 36 is supplied with alternating voltages from wires 40 which extend from a drive circuit which is mounted on a printed circuit board 42. The printed circuit board is also supported on the upper side of the chassis 24.

A multi-position switch 44 is mounted to the underside of the printed circuit board 42. The switch 44 includes a switch element 46 which is moveable along a horizontal linear path A—A (FIG. 2) to any of several positions. The switch is connected to the circuits on the printed circuit board 42 such that by moving the switch element 46 to a particular position, a corresponding rate of atomization will occur. In a particular design the switch 44 controls a duty cycle wherein atomization occurs for 50 millisecond intervals with the time between successive intervals being adjustable between, for example, 5 and 40 seconds.

An elongated switch arm 48 is pivotally mounted at one end by means of a pivot 50 on the chassis 24. The pivot 50 has a pivot axis 50a which is vertical so that the arm 48 also swings along a horizontal curved path B—B (FIG. 2). The arm 48 extends from the pivot 50 and out through the horizontal slot 18 in the outer cover 12 where it is connected to the actuator button 20. Because the arm 48 is mounted on the chassis 24 by means of the pivot 50, it is not guided by the sides of the slot 18 nor does it ride on or obtain support from the cover 12. As can be seen in FIGS. 2 and 3, the switch arm 48 extends under the switch 46; and as seen in FIG. 2, the range of movement of the arm 48 is such that it sweeps over the entire path of linear movement of the switch element 46.

The switch arm 48 is connected to the switch element 46 by a lost motion mechanism 51 which, as shown in FIGS. 2 and 3, comprises a pair of lug elements 52 which are fixed to the arm 48 and extend upwardly therefrom and along each side, respectively, of the switch element 46. Movement of the switch arm 48 along the curved path A is communicated by the lug elements 52 to the switch clement 46 to move the switch element along the linear path B. It will be seen that the lost motion mechanism 51 permits relative movement between the switch arm 48 and the switch element 46 in a direction perpendicular to the linear path A of the switch element but it prevents relative movement between the switch arm and the switch element is a direction parallel to the path A. Thus, the switch actuator button 20 can be moved along the curved path B path while the switch arm 48 moves the switch clement 46 along the linear path B to each of its several switch positions.

Because the switch actuator button 20 is mounted on the switch arm 48, it is supported entirely by the switch arm which in turn is supported on the chassis 24 via the pivot 50. As a result no mechanical interconnection is needed between the outer cover 12 and the switch arm 48 or the switch actuator button 20. Accordingly the cover 12 does not need to be reinforced to support the button 20 or the switch arm 48 and there is no danger of interference between the cover and the switch arm which might otherwise be caused by bending of the cover as the switch arm is moved.

It will be appreciated that other forms of a lost motion mechanism can be used to convert the curvilinear movement of the switch arm 48 to the linear movement of the switch actuator 46. For example, the lug elements 52 could be fixed to the switch element 46 and extend to the switch arm 48, or a single lug could be fixed to and extend from one of the switch element 46 and the switch arm 48 and extend therefrom into a slot formed in the other member. In such case the slot would extend in a direction which is generally perpendicular to the path A of movement of the actuator element 46.

INDUSTRIAL APPLICABILITY

This invention permits a switch arm of an adjustable device to be mounted in a manner that does not put a strain on the outer cover of the device and that does not lead to a problem of interference or jamming as the switch arm is moved.

What is claimed is:

1. A switch actuating mechanism comprising:
   an elongated switch arm pivotally mounted at one end thereof on a support;
   a switch having a switch element which is moveable along a linear path, said switch being mounted in a fixed position relative to said support; and
   a lost motion interconnection between said switch arm and said switch element, said lost motion interconnection being constructed to permit relative movement between said switch element and said switch arm in a direction perpendicular to said linear path and to prevent relative movement between said switch arm and said switch element in a direction parallel to said linear path,
   whereby pivotal movement of said switch arm produces linear movement of said switch element.

2. A switch actuating mechanism according to claim 1, wherein said switch arm pivots about an axis that is perpendicular to said linear path.

3. A switch actuating mechanism according to claim 2, wherein said switch element is moveable through a given range along said linear path.

4. A switch actuating mechanism according to claim 3, wherein said switch arm pivots through an arc which extends over said given range.

5. A switch actuating mechanism according to claim 4, wherein said lost motion interconnection comprises at least one element which extends between said switch arm and said switch element, said at least one element being fixed to one of said switch arm and said switch element and exerts force in a lateral direction on the other of said switch arm and said switch element while allowing free relative movement in a longitudinal direction.

6. A switch actuating mechanism according to claim 5, wherein a pair of elements extend from said switch arm to sides of said switch element.

7. A switch actuating mechanism according to claim 1, wherein said switch arm extends beyond said lost motion interconnection and out through a slot in an outer cover.

8. A switch actuating mechanism according to claim 7, wherein said outer cover has a curved outer surface.

9. A switch actuating mechanism according to claim 8, wherein said curved outer surface has a center of curvature at said pivot axis.

10. An electrically controlled device comprising:
    a mechanism for producing a desired result;
    an electrical circuit connected to control operation of said mechanism, said electrical circuit including a multi-position switch having a switch element which is moveable through a given range along a linear path;
    a support structure on which said electrical circuit and said switch are mounted;
    an outer cover which encloses said electrical circuit, said switch and said support structure;
    an elongated switch arm pivotally connected at one end thereof to said support structure inside said outer cover such that said switch arm pivots about an axis that is perpendicular to said linear path and such that said switch arm can swing through an arc that includes said given range; and
    a lost motion mechanical interconnection between said switch arm and said switch element and located within said outer cover, said lost motion interconnection being constructed to permit relative movement between said switch element and said switch arm in a direction perpendicular to said linear path and to prevent relative movement between said switch arm and said switch element in a direction parallel to said linear path,
    said switch arm extending beyond said interface and out through a slot in said outer cover.

11. An electrically controlled device according to claim 10, wherein said lost motion mechanical interconnection comprises at least one element which extends between said switch arm and said switch element, said at least one element being fixed to one of said switch arm and said switch element and exerts force in a lateral direction on the other of said switch arm and said switch element while allowing free relative movement in a longitudinal direction.

12. An electrically controlled device according to claim 11, wherein a pair of elements extend from said switch arm to sides of said switch element.

13. An electrically controlled device according to claim 10, wherein said outer cover has a curved outer surface.

14. An electrically controlled device according to claim 13, wherein said curved outer surface has a center of curvature at said pivot axis.

* * * * *